United States Patent [19]
Abdel-Rahman

[11] Patent Number: 6,037,179
[45] Date of Patent: Mar. 14, 2000

[54] METHOD AND APPARATUS FOR SUPPRESSION OF ANALYTE DIFFUSION IN AN IONIZATION DETECTOR

[75] Inventor: Mahmoud F. Abdel-Rahman, West Grove, Pa.

[73] Assignee: Hewlett-Packard Company, Palo Alto, Calif.

[21] Appl. No.: 09/070,043

[22] Filed: Apr. 30, 1998

[51] Int. Cl.[7] .................................................. G01N 1/22
[52] U.S. Cl. ........................... 436/52; 436/153; 436/174; 436/181; 422/83; 422/103
[58] Field of Search .............................. 436/43, 52, 153, 436/174, 176, 180, 181; 422/63, 81, 83, 98, 103; 73/864.81, 864.85, 863

[56] References Cited

U.S. PATENT DOCUMENTS

| | | | |
|---|---|---|---|
| 4,542,293 | 9/1985 | Fenn et al. | 250/288 |
| 4,684,807 | 8/1987 | Wells | 250/381 |
| 4,780,284 | 10/1988 | Lovelock | 422/83 |
| 4,789,783 | 12/1988 | Cook . | |
| 4,861,355 | 8/1989 | Macrow | 55/127 |
| 4,975,648 | 12/1990 | Lawson et al. . | |
| 5,028,544 | 7/1991 | Rasulev et al. | 436/161 |
| 5,153,519 | 10/1992 | Wentworth et al. . | |
| 5,256,374 | 10/1993 | De Silva et al. | 422/80 |
| 5,317,271 | 5/1994 | Wentworth et al. . | |
| 5,394,090 | 2/1995 | Wentworth et al. . | |
| 5,394,091 | 2/1995 | Wentworth et al. . | |
| 5,394,092 | 2/1995 | Wentworth et al. . | |
| 5,528,150 | 6/1996 | Stearns et al. . | |
| 5,532,599 | 7/1996 | Stearns et al. . | |
| 5,541,519 | 7/1996 | Stearns et al. . | |
| 5,544,540 | 8/1996 | Meng | 436/153 |
| 5,594,346 | 1/1997 | Stearns et al. . | |
| 5,689,111 | 11/1997 | Dresch et al. | 250/287 |

OTHER PUBLICATIONS

G. Gremaud, W. E. Wentworth, A. Zlatkis, R. Swatloski, E.C.M. Chen, S. Stearns, "Windowless Pulsed–Discharge Photoionization Detector Application To Qualitative Analysis Of Volatile Organic Compounds", accepted Aug. 18, 1995, Journal of Chromatography A. 724 (1996) pp. 235–250.

Herbert H. Hill and Dennis G. McMinn, Dept. of Chemistry, Washington State University, Pullman, Washington; "Detectors for Capillary Chromatography"; Chemical Analysis Series, vol. 121; ISBN 0–471–50645–1; 1992 John Wiley & Sons, Inc.

Primary Examiner—Long V. Le

[57] ABSTRACT

Method and apparatus are disclosed for improved transfer of ionizing particles from a source chamber to a detection zone in an ionization chamber in an ionization detector. An ionization detector includes a source chamber, an inlet for introducing detector gas to the source chamber, a transitional structure including a flow guide that directs detector gas flow between the source chamber and the adjacent ionization chamber, an inlet for introducing sample gas containing an analyte into the ionization chamber, and an outlet port for exhausting the mixture of the sample gas and the detector gas. The aspect ratio of the flow guide causes the linear velocity of the detector gas stream to be highest at a throat in the flow guide and to decrease as the detector gas stream approaches a detection zone in the ionization chamber, thereby suppressing analyte diffusion from the ionization chamber through the flow guide. The aspect ratio of the flow guide also provides an unimpeded path for transit of photons from the source chamber to the detection zone in the ionization chamber.

12 Claims, 7 Drawing Sheets

METHOD AND APPARATUS FOR SUPPRESSION OF ANALYTE DIFFUSION IN AN IONIZATION DETECTOR

FIELD OF THE INVENTION

This invention relates generally to detectors for analysis of a sample gas; and more particularly, to an ionization detector having apparatus for more efficient production and use of ionizing particles such as metastables and photons.

BACKGROUND OF THE INVENTION

Figure 1:
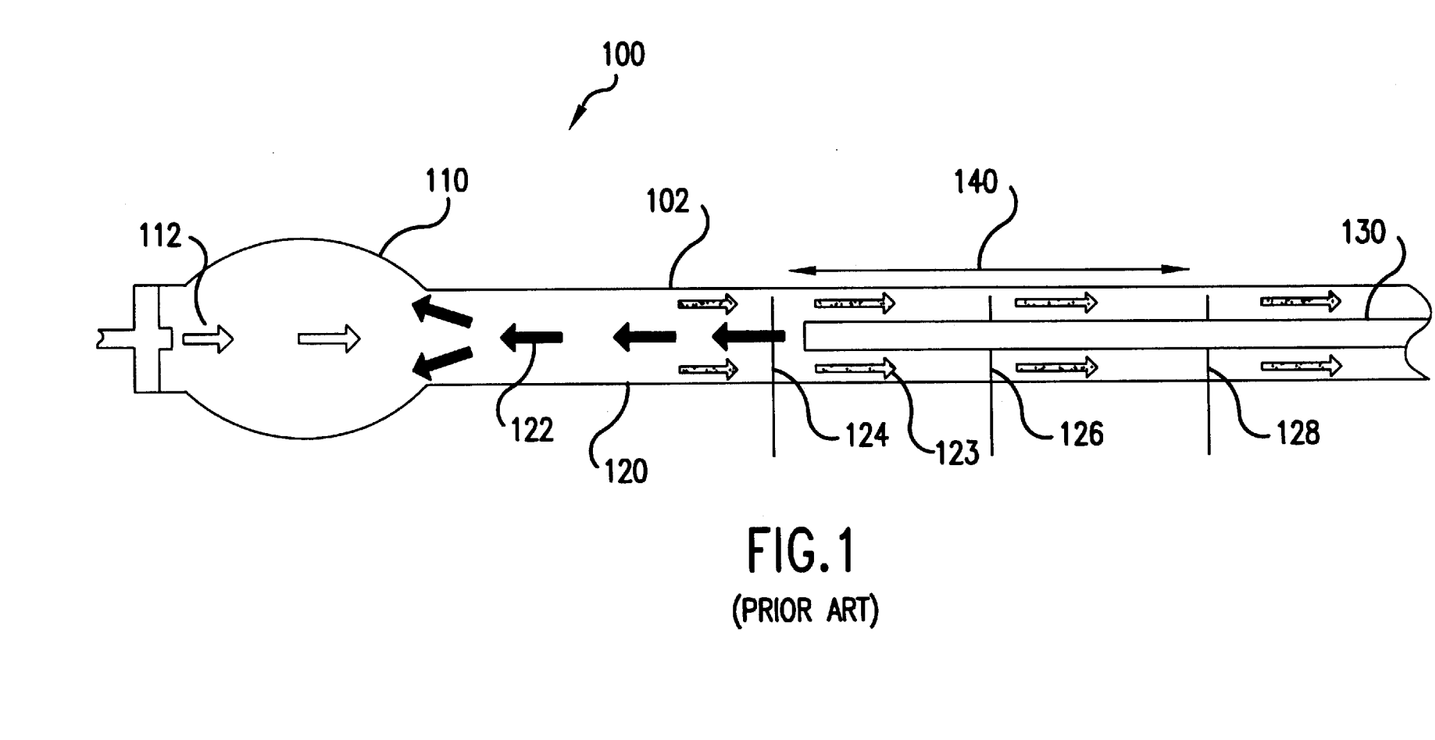
FIG. 1 is a simplified schematic view of a conventional ionization detector constructed according to the prior art.

As illustrated in FIG. 1, an ionization detector 100 typically comprises a body 102 having a first chamber 110 for generation of ionizing particles and a second chamber 120 connected to the first chamber 110 for receiving a sample gas 122. The sample gas 122 is conveyed in a carrier gas and is provided to the second chamber 120 by a conduit 130 which typically is provided in the form of a separation column. The first chamber 110 includes a source of ionizing particles (not shown), such as a radioactive source or an electrical discharge, and is typically swept by a detector gas 112 selected from the class of known noble gases. The presence of the detector gas 112 in the first chamber 110 causes ionizing particles, in the form of photons and metastables, to be produced. The flow of the detector gas 112 from the first chamber 110 to the second chamber 120 causes the ionized particles to be mixed with the sample gas 122, thus causing the sample molecules of interest, considered herein as analytes, to be ionized. The second chamber 120 includes electrodes 124,126,128 located in a detection zone 140 for detecting the ionized sample molecules by use of an electrometer (not shown) connected to the electrodes 124,126, 128.

Detector sensitivity may be measured in a plot of detector response versus analyte concentration or analyte quantity. The range over which the detector sensitivity is constant is called the linear dynamic range, and the entire range over which the response is variable with analyte concentration or quantity is called the dynamic range of the detector. The upper limit of the dynamic range is determined when detector sensitivity falls to an unusable value, typically zero, and the detector is said to be saturated. The lower limit of the dynamic range occurs at a minimum detectable level (MDL).

Particular examples of ionization detectors include the electron capture detector and the discharge ionization detector.

Electron capture detectors for gas chromatography are well known in the art. This type of detector offers high sensitivity and high selectivity towards electrophilic compounds and is widely used for detecting trace amounts of pesticides in biological systems and in food products. Such compounds typically contain halogens which combine with free electrons that are created in the ionization chamber in the detector. The resulting decrease in free electrons in the ionization cell is monitored as an indication of the concentration of the compounds in a sample.

A discharge ionization detector operates by applying a high voltage across discharge electrodes that are located in a gas-filled source chamber. In the presence of a detector gas such as helium, a characteristic discharge emission of photons occurs. The photons irradiate an ionization chamber receiving a sample gas that contains an analyte of interest. Ions are produced in the ionization chamber as a result of photon interaction with ionizable molecules in the sample gas. Helium metastables are also generated in the source chamber and are found to play a role in ionization of the analyte of interest.

Figure 2:
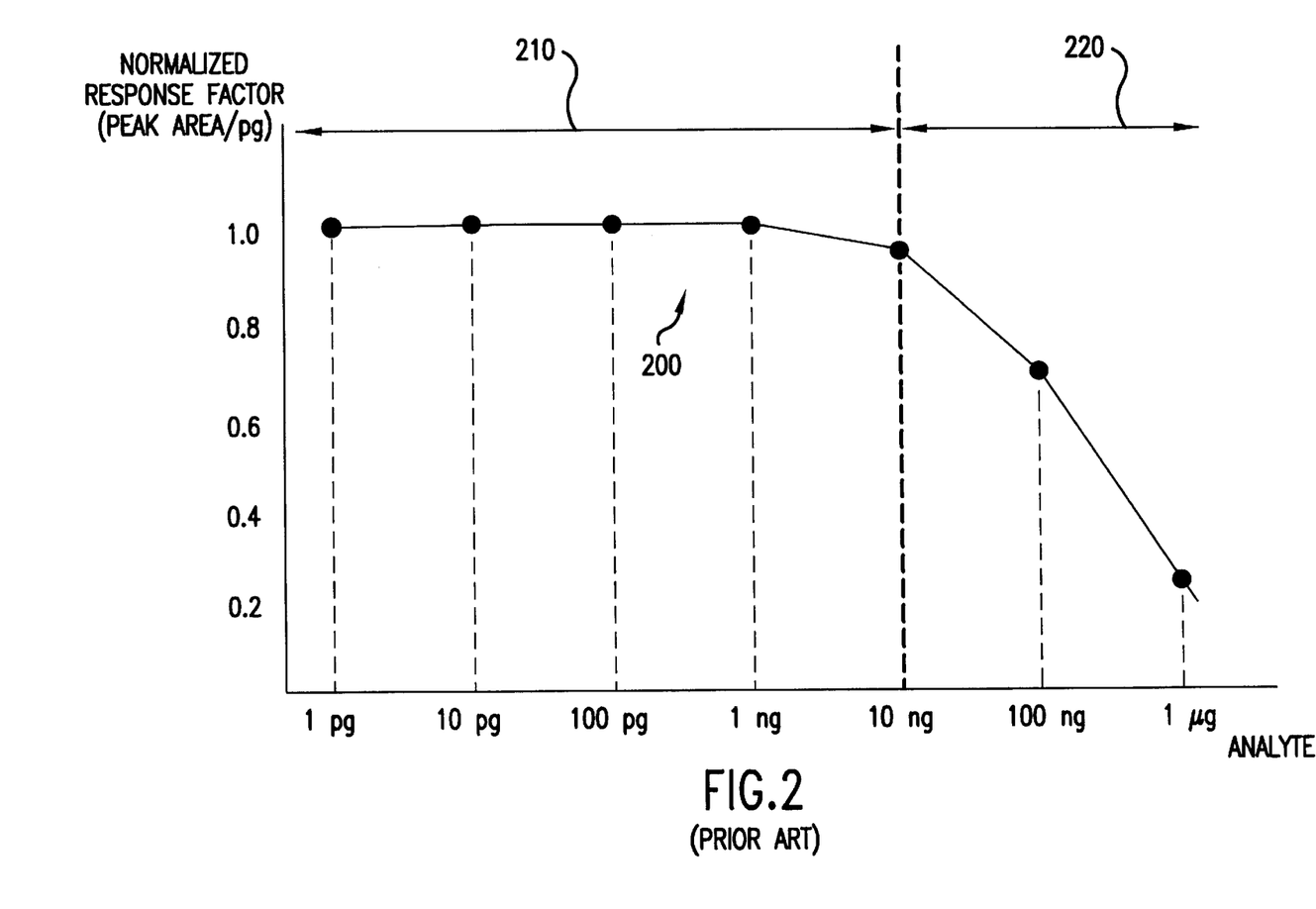
FIG. 2 is a graphical representation of the normalized response factor exhibited by a conventional ionization detector of the prior art.

FIG. 2 illustrates a linearity plot 200 that is typical of the dynamic range of a helium discharge ionization detector. The magnitude of the ionized analyte molecules is manifested as a current that can be measured to ascertain the composition of one or more analytes. In the illustrated linearity plot, the analyte is carbon-12 ($C_{12}$). The response factor should ideally be constant (in other words, flat) irrespective of the amount of the analyte introduced into the detector. As illustrated, the response factor is flat over the linear dynamic range 210 but decreases in a second region 220 when higher amounts of analyte are introduced to the detector.

Although the design of ionization detectors continues to be an object of study in the prior art, there nonetheless exists a need for an ionization detector having a detector response that exhibits an improved dynamic range, lower minimum detectable level (MDL), and a greater signal to noise ratio.

SUMMARY OF THE INVENTION

The present invention is directed to an ionization detector having an improved dynamic range, lower minimum detectable level (MDL), and a greater signal-to-noise ratio in the detector response.

Detector response in an ionization detector is based on an accurate measurement of the ionized analyte of interest. More efficient generation of metastables and photons in a volume of noble gas will therefore improve certain characteristics of the detector response, such as the minimum detectable level (MDL), and signal-to-noise ratio.

I have found that conventional ionization detectors suffer from a loss of such metastables and photons when analyte molecules are allowed to diffuse away from a detection zone in an ionization chamber toward the source of ionization particles in a source chamber (such movement of analyte molecules is hereinafter described as analyte diffusion). Analyte diffusion allows the analyte molecules to combine with the ionizing particles at points located well upstream of the detection zone. As a result, fewer analyte molecules are detected in the detection zone and fewer ionizing particles can progress to the detection zone. When there is a high concentration of analyte molecules in the ionization chamber, the number of ionizing particles that reach the detection zone becomes significantly less, and the detector response is unstable or nonlinear.

As a result of my findings, I have discovered an opportunity to achieve improved dynamic range, lower minimum detectable level (MDL), and greater signal to noise ratio in the detector response by suppressing the analyte diffusion and improving the transfer of metastables and photons to the detection zone in an ionization detector.

The present invention is directed to an ionization detector having an ionization chamber, a source chamber, and a novel transitional structure situated therebetween that has been found to suppress analyte diffusion, and particularly to an ionization detector having a source chamber, an ionization chamber, and a transitional structure having a diverging bore, all of which are integrated in a common detector body. Preferably, the invention contemplates the use of a source chamber having a source of ionizing particles and receiving a fluid stream of detector gas (preferable selected from a group of noble gases, and most preferably being helium or argon). The detector gas stream flows through the source chamber and into the ionization chamber so as to allow metastables and photons to be generated in the source chamber and to be transferred to a detection zone in the ionization chamber. A spaced array of electrodes are situated in the ionization chamber and thereby define the detection zone. In addition, the transitional structure has a diverging bore so as to promote a region of high linear velocity of the detector gas stream during the transition of such detector gas stream from the source chamber into the ionization chamber, and a region of low linear velocity of the detector gas stream in the vicinity of a detection zone wherein the ionized analyte molecules may be subject to measurement with use of an electrometer. As a result, the desired transition of the metastables and photons into the ionization chamber occurs, while little or no analyte diffusion occurs. There is a greater abundance of metastable and photons in the detection zone, where they play an important role in the desired ionization of analyte molecules present in a sample gas provided to the ionization chamber.

In one embodiment of the present invention, there is provided an ionization detector that employs an ionization chamber, a source chamber, and a transitional structure for promoting the transition of ionizing particles from the source chamber to the ionization chamber for ionization of an analyte present in the ionization chamber, wherein the transitional structure includes a flow guide defined by a diverging portion of the interior wall of the common detector structure. The inner cross section of the flow guide increases in accordance with the downstream progress of the detector gas stream, whereby the flow guide allows fluid communication between the source chamber and the ionization chamber. The flow guide causes the linear velocity of the detector gas stream to be reduced as the detector gas stream progresses to the detection zone. The desired region of high linear velocity in the transitional structure is thereby located well upstream of the detection zone.

In a particularly preferred embodiment, the flow guide is provided in the form of a conical horn, whereby the flow guide is defined by a diverging portion of the interior wall of the common detector structure. The inner cross section of the flow guide increases in accordance with the downstream progress of the detector gas stream, that is, towards the detection zone, such that the linear velocity of the detector gas stream that exits the source chamber is higher than the linear velocity of the detector gas stream entering the detection zone. Preferably, the conical horn has its apex located at the boundary between the transitional structure and the source chamber (and such apex also being described herein as the throat of the transitional structure), whereby a first linear velocity of the detector gas stream within the throat is gradually reduced to a second linear velocity that is substantially less than the first linear velocity. The second linear velocity of the detector gas stream is substantially less than the first linear velocity so as to increase the residency time of metastables and photons in the detection zone, thus to better effect ionization of the analyte.

In another embodiment of the invention, the transitional structure includes a detector gas flow restriction situated between the source chamber and the ionization chamber that causes the linear velocity of the detector gas stream in the throat to increase as it passes from the source chamber into the ionization chamber. The desired region of high detector gas flow rate is provided by the flow restriction, preferably formed in the throat, so as to cause the original flow rate of the detector gas stream, as it exits the source chamber, to be highest at the point of the detector gas stream entry into the transitional structure. As a result, the flow rate of the detector gas stream is highest in the throat, thus creating the desired region of high linear velocity, and thereby creating a pressure differential between the source chamber and the ionization chamber, thereby suppressing the potential diffusion of analyte through the transition structure from the ionization chamber to the source chamber.

In another aspect of the invention, the throat section and the conical horn are provided in a coaxial, continuous, seamless structure, wherein the ionizing particles are rapidly swept into the ionization chamber without encountering eddy currents or discontinuities. The abundance of metastables placed in the ionization chamber prior to decay is then effective at improving the desired ionization of the analytes of interest.

In another aspect of the invention, ionization is particularly enhanced by provision of a conical horn that functions as the major portion of the interior wall of the ionization chamber, and which exhibits a sufficient cone angle to allow a useful line-of-sight path from a point within the source chamber to the detection zone in the ionization chamber, such that the majority of the photons that are generated within the source chamber can traverse this unimpeded path from the point to the detection zone without premature decay due to one or more collisions with the interior side wall of the ionization chamber. For the purposes of this description, the majority of the photons are considered as being generated at a point upstream of the apex of the conical horn, and such point herein is defined as the point ionization source, so as to allow a line-of-sight propagation of the photons from the point ionization source to the detection zone. The abundance of photons that enter the detection zone unimpeded and prior to decay is then more effective at ionizing the analyte molecules of interest.

In another embodiment of the invention, a stream of a sample gas, preferably containing an analyte of interest transported within a conduit via a carrier fluid stream, is provided into the ionization chamber by a conduit-receiving structure mounted to a side wall of the ionization chamber so as to cause the major axis of such conduit to be transverse to the general direction of the detector gas stream into the ionization chamber. The conduit-receiving structure includes a fitting for receiving the outlet end of the conduit and for positioning the tip of the outlet end of the conduit within a plane defined by the side wall of the ionization chamber. The tip of the outlet end of the conduit is thereby recessed from to the majority of the detector gas stream, and hidden from the line of sight from the point ionization source into the ionization chamber. As a result, the detector gas stream is less likely to encounter a countervailing stream of sample gas from the conduit. Additionally, the outlet end of the conduit is not positioned within the transit of photons that radiate from the ionization point source, and is therefore less susceptible to physical degradation due to the impingement of such photons. In a preferred embodiment, the conduit is provided in the form of a separation column known for use in gas chromatography. As a result, the contemplated detector is less susceptible to contamination due to the photon-induced vaporization of materials typically present in a separation column such as a protective coating, often formed of polyimide, or a stationary phase, either of which is typically present on a conventional separation column. Such contamination, which causes an increase in the baseline current of the detector, is quite undesirable. Such an increase in the baseline current, and the corresponding time required for stabilization of the baseline current are minimized.

According to another preferred embodiment of the invention, there is provided a source chamber, a transitional structure, and an ionization chamber located in common structure, a detector gas port for introducing a detector gas fluid into the source chamber, a transitional structure having a flow guide that directs a detector gas stream from the source chamber to a detection zone in the adjacent ionization chamber, a conduit receiving structure for receiving a conduit, such as a separation column, and for introducing therefrom a flow of sample gas containing an analyte into the ionization chamber, and a vent for venting a mixture of the sample gas and the detector gas from the ionization chamber. The flow guide promotes the flow of ionization particles such as metastables into the ionization chamber and suppresses the analyte diffusion into the source chamber. The interior wall of the flow guide forms a conical horn to promote a line of sight transfer of photons in the flow guide from the source chamber to the ionization chamber.

In another particular embodiment, the ionization chamber includes a signal measuring circuit having a signal electrode assembly positioned in the ionization chamber; a plurality of electrodes in the electrode assembly is biased in a detector circuit with an electrometer. Under appropriate conditions, the presence of analyte compounds in the ionization chamber alter the current flow between the electrodes. The resulting change in current flow is a measure of the presence of constituent(s) in the analyte. In particular, one preferred electrode assembly may be constructed to include a signal cathode mounted in an insulating sleeve in the detector body so as to project into the ionization chamber. A signal monitoring circuit may be constructed to include the signal cathode, a connection to the ionization chamber wall such that the ionization chamber wall acts as an electrode, means for biasing the signal cathode and the ionization chamber wall for generating an electric field with respect to the exposed portion of the signal cathode to cause positively-charged analyte ions to be accelerated toward the ionization chamber wall, and an electrometer for providing an indication of the analyte ionic current flow between the signal cathode and the ionization chamber wall so as to indicate the amount of ionized analyte components in the sample gas.

According to another preferred embodiment of the invention, an ionization detector in accordance with the present invention may be constructed to include a detector body defining a first chamber in the form of a source chamber and a second chamber in the form of an ionization chamber, these first and second chambers being coaxially disposed and having an aperture there between in a common internal wall, and wherein the majority of the ionization chamber is provided in the form of a conical horn. The body includes an inlet to the source chamber for admitting a detector gas, preferably provided in the form of a pressurized stream of helium, and a column receiving structure having an inlet to the ionization chamber for admitting a flow of sample gas to be analyzed.

In another preferred embodiment of the invention, the source chamber includes a discharge source having located so as to enable the creation of a discharge in the discharge source in close proximity to the desired point ionization source and to the throat of the transitional structure. In this preferred embodiment, the discharge cathode is coaxially mounted with respect to the aperture between the source chamber and the transitional structure. The discharge is rapidly and effectively swept by the flow of the detector gas into the throat and then to the ionization chamber. Metastables and photons generated in the discharge are thereby effectively transferred into the ionization chamber for improved ionization of species in the column effluent.

In another preferred embodiment of the invention, the source chamber includes a ionizing particle source having a radioactive material which is situated in at least one side wall of the source chamber. The ionizing particle source is located so as to enable the creation of a plurality of ionizing particles in close proximity to the desired point ionization source and to the throat of the transitional structure.

Accordingly, an ionization detector may be constructed wherein the detector response is characterized by improved measurement of analyte concentration, that is, a lower minimum detectable level of analyte concentration, and by an increased dynamic range.

BRIEF DESCRIPTION OF THE DRAWINGS

The foregoing and other features and advantages of the invention will be apparent from the following more particular description of preferred embodiments of the drawings, in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

The apparatus and methods of the present invention may be employed in particular to improve the detection of an analyte that may be present in a variety of fluids. Gases are the preferred fluids according to the practice of the present invention, and therefore the following description of the invention will include a description of the arrangement, construction, and operation of a novel discharge ionization detector for use in a gas sample analytical system. The teachings of this invention apply to any detector operating on the principle of ionization of a fluid mixture, and as such include a discharge ionization detector, helium ionization detector, argon ionization detector, electron capture detectors, and other detectors having either radioactive or non-radioactive ionization particle sources.

One particular application of the novel discharge ionization detector is in a chromatographic analytical system (hereinafter, a chromatography); however, other applications such as process sampling systems, gas leak detection systems, air quality monitoring systems, and the like are contemplated.

For the purposes of the description herein, certain terms are defined as follows:

A detector gas may be considered to include a gas selected for the purpose of generating ionizing particles in a source chamber, and is preferably selected from the class of gases known as the noble gases. The preferred detector gas may include a mixture of one or more noble gases. A preferred noble gas is helium.

A source of ionizing particles may be considered to include an electrical discharge source such as is known in a discharge ionization detector, a photo ionization source, or a radioactive source.

Ionizing particles may be considered to include photons and metastables.

A conical horn may be considered to include a tube of finite length and of varying cross section, in which the area of cross section increases according to distance along the horn axis from a chosen origin (considered herein as the apex). Such cross sectional area may be considered to increase according to a linear, exponential, parabolic, or similar factor. Preferably, the conical horn has a circular cross section, although rectilinear (e.g., square, trapezoidal, or rectangular) and ellipsoidal cross sections are contemplated as well.

Embodiments of the invention described herein are contemplated for use as an ionization detector, and in particular in a discharge ionization detector or in an electron capture detector, in a gas chromatograph.

Figure 3:
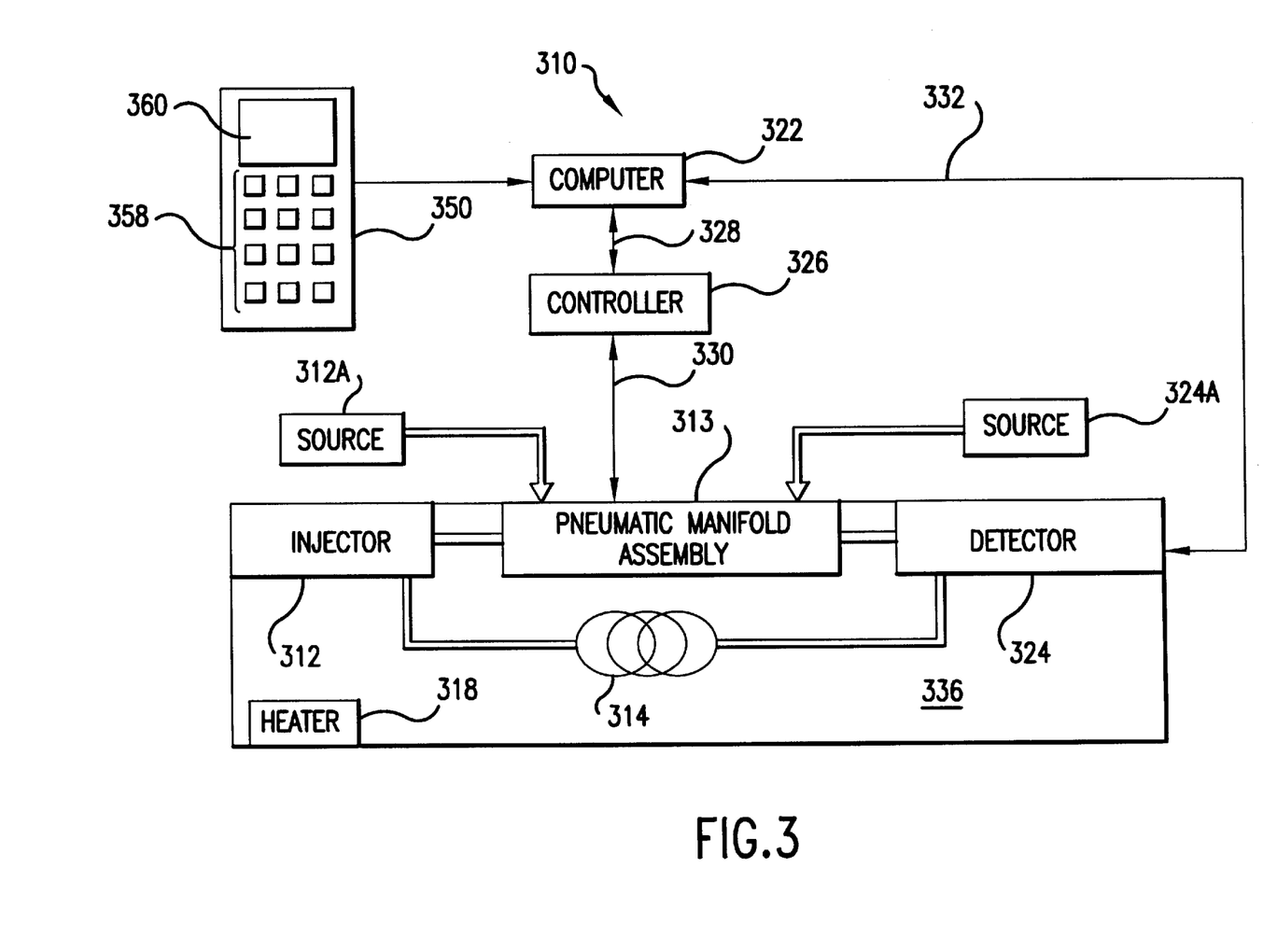
FIG. 3 is a simplified schematic representation of an analytical instrument having therein an improved ionization detector constructed according to the present invention.

A novel ionization detector may be designed for use in an analytical instrument as shown in FIG. 3. The instrument is generally designated chromatograph 310. In the preferred embodiment, the chromatograph 310 is a Hewlett-Packard HP6890 gas chromatograph that is modified to include a novel ionization detector 324 constructed according to the teachings herein.

Operation of the chromatograph 310 may be generally understood as follows. In order to perform a chromatographic separation of a given sample compound, a sample is injected with a pressurized carrier gas by means of an injector 312. The carrier gas supplied to injector 312 is provided from a source 312A through one or more pneumatic manifold assemblies 313, each of which serves in part to control and redirect a plurality of gas flows, including the carrier gas and one or more detector gas of appropriate types. The detector gas are provided from respective sources (one such source 324A is shown) to the pneumatic manifold assembly 313. Suitable fluid-handling devices such as valves, sensors and the like in the pneumatic manifold assembly 313 are operated under the control of the computer 322 and controller 326 by way of control signals provided on a data and control lines 328, 330, 332. The control and data line 330 also allows the return of sense information from suitable sensors and signal-interface electronics that are provided in the pneumatic manifold assembly 313. Another set of data and control lines 332 allows the transfer of detector output signal information between the detector 324 and the computer 322.

A separation column 314 is positioned within an oven 336. The carrier gas/sample combination passing through column 314 is exposed to a temperature profile resulting in part from the operation of a heater 318 within oven 336. During this profile of changing temperatures, the sample will separate into its components primarily due to differences in the interaction of each component with the column 314 at a given temperature. As the components exit column 314 they are detected by the detector 324.

Computer 322 maintains overall control of the systems associated with chromatograph 310. It will be recognized that any particular gas chromatograph may include more systems than those described in relation to the present invention. For example, an electronic control panel 350 is shown to include an operator interface provided in the form of a keypad 358 and a display 360. It will also be understood that although computer 322 is shown as a single block, other embodiments are contemplated; for example, the functions of the computer 322 may be subsumed into one unit. The computer 322 includes a central processing unit and all associated peripheral devices, such as random access memories, read-only memories, input/output isolation devices, clocks, and, preferably, a digital signal processing unit, and other related electronic components. In the preferred embodiment, the central processor used in computer 322 is a microprocessor.

Figure 4A:
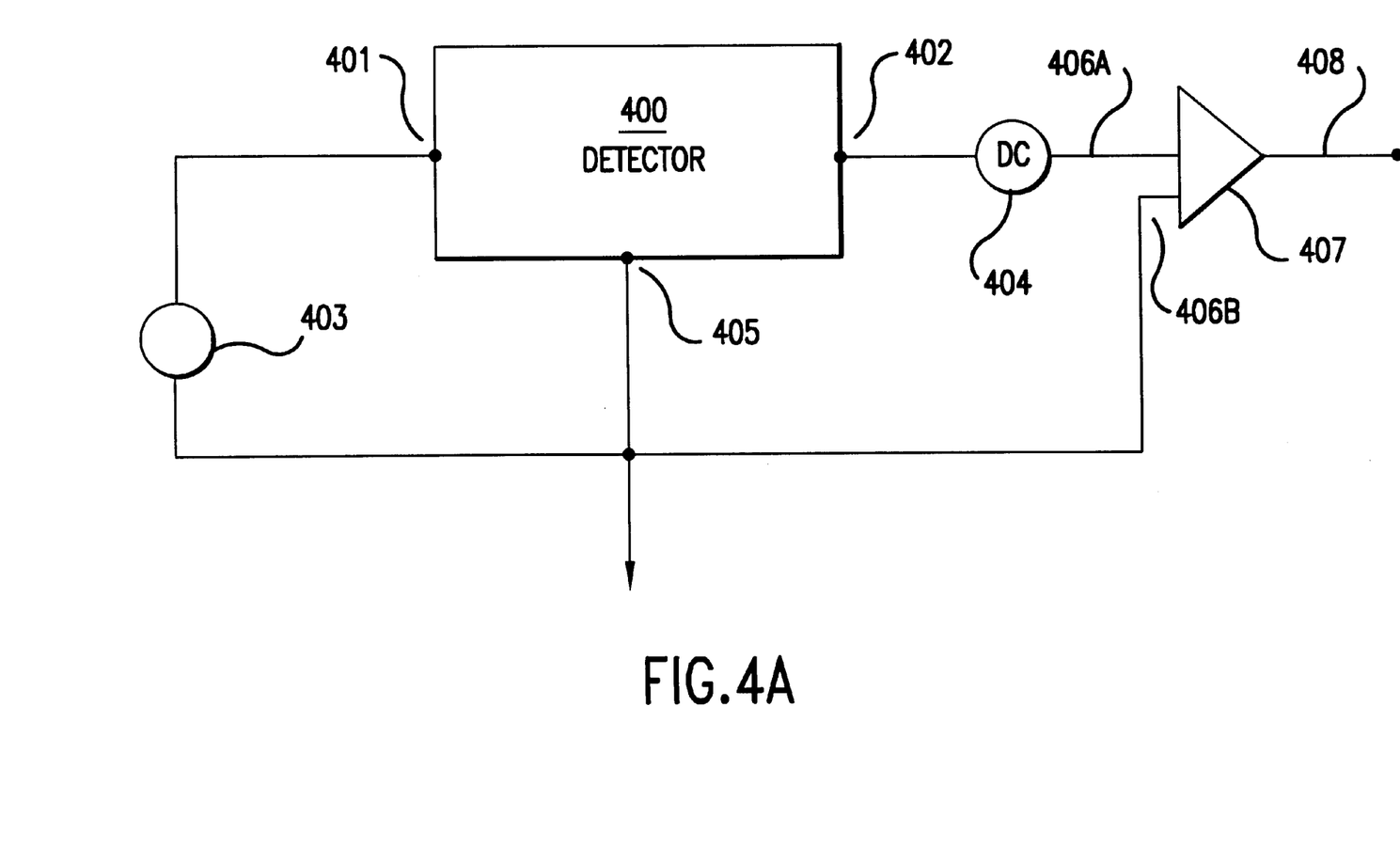
FIG. 4A is a schematic of a detector circuit including the ionization detector of FIG. 3.

As illustrated in FIG. 4A, a preferred embodiment 400 of a ionization detector may be constructed according to the invention to include a discharge cathode connector 401 connected in series to a discharge voltage supply 403. (Alternatively, the preferred embodiment 400 may be constructed according to the invention to include a radioactive source material in lieu of a discharge source for provision of ionizing particles, and accordingly the discharge cathode connector 401 and the discharge voltage supply 403 may be omitted.) The detector further includes a signal cathode connector 402, a signal bias voltage supply 404, and a common connector 405 (which is connected to a ground potential). Differential inputs 406A, 406B in an electrometer 407 may be connected to the signal bias voltage supply 404 and the common connector 405 so as to provide a detector output signal on a detector output signal line 408 for measuring the current passing between the signal cathode connector 402 and the common connector 405.

Figure 4B:
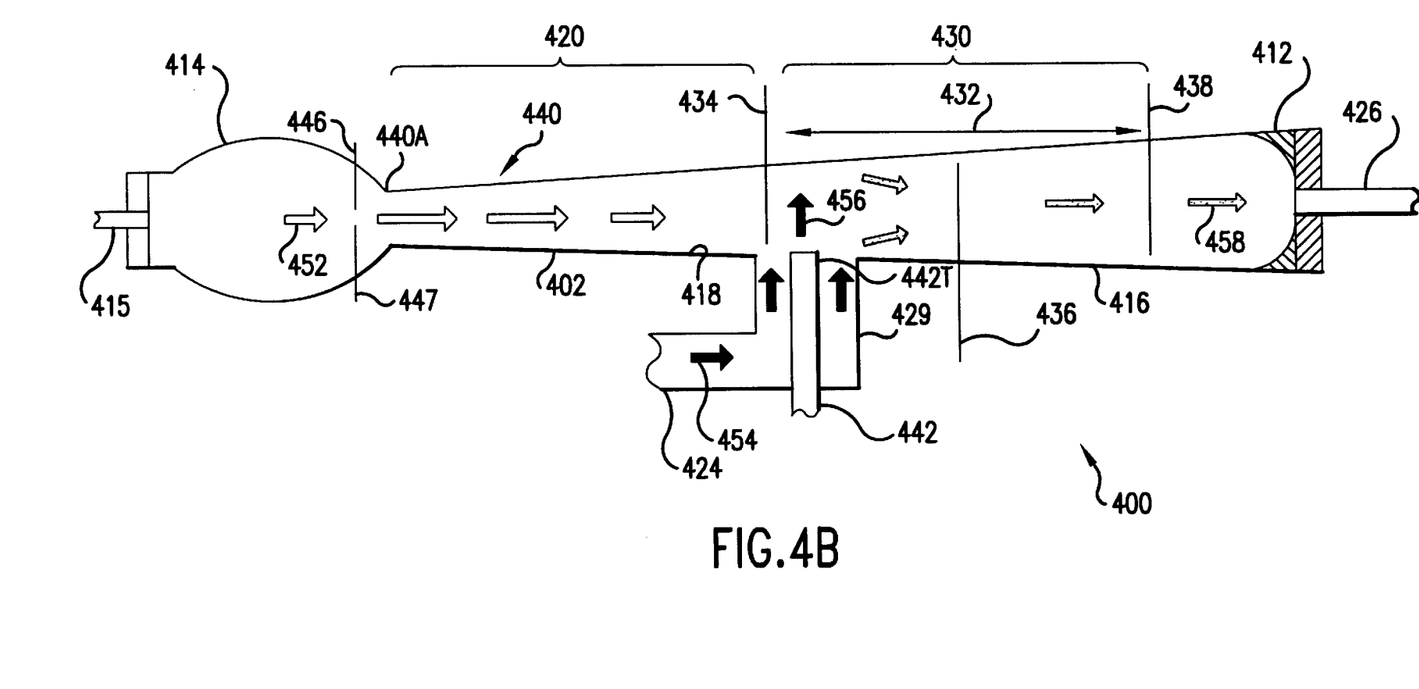
FIG. 4B is a simplified cross-sectional view of one embodiment of the ionization detector of FIG. 3.

As illustrated in FIG. 4B, the preferred embodiment 400 is constructed to include a detector body 412 defining first and second adjacent chambers, preferably constructed as source chamber 414 and ionization chamber 416, respectively, which are joined by a transitional structure 420. The transitional structure 420 and the ionization chamber 416 share a common internal wall 418 which is preferably provided in the shape of a conical horn. The source chamber 414 includes a source of ionizing particles such as a discharge electrode assembly including discharge electrodes 446.447. (Alternatively, a radioactive material may be provided as a source of ionizing particles in the source chamber 414 in lieu of the discharge electrode assembly, as may be selected and constructed by those skilled in the art.) The volume of the ionization chamber 416 is preferably in the range of 10 to 100 microliters and in some applications may be less than 2 microliters and as large as 1,000 milliliters. The detector body 412 includes inlet 415 for admitting a controlled flow of detector gas, preferably one of the noble gases such as helium, and an inlet 424 to the ionization chamber 416 that includes a column receiving structure 429 for receiving a conduit 442. In the illustrated embodiment, the detector body 412 is preferably of unitary construction having the discharge and ionization chambers 414, 416 provided in an electrically insulating and chemically inert material such as quartz, high-purity ceramic material, or silica according to known construction techniques. Preferably, the conduit 442 is provided in the form of a conventional separation column for admitting a sample gas having an analyte therein to be detected.

In the preferred embodiment, the column receiving structure 429 is constructed to direct the effluent flow of sample gas into a detection zone 432 in a direction that is transverse to the oncoming fluid stream of detector gas entering the detection zone 432 from the transitional structure 420; as will be appreciated in light of the description below, other configurations of the column receiving structure 429 are less advantageous, but are nonetheless within the scope of the present invention. Vent outlet 426 is situated at an opposing end of the ionization chamber 416. The detection zone 432 is generally defined by the location of a signal electrode assembly 430. The signal electrode assembly 430 preferably includes a collector electrode 436 and first and second signal electrodes 434,438. The signal electrode assembly 430 is connected, by way of an appropriate electrical connector (not shown) to a voltage potential applied between the collector electrode 436 and both of the first signal electrode 436 and second signal electrode 438.

The electrode assembly 430 provides an electric field so as to define the detection zone 432. The electrode assembly 430 may be coupled to an electrometer (not shown) by appropriate means, so as to provide for an indication of the amount of ionized components present in the detection zone 430.

In the illustrated embodiment, the electrodes 434, 436, 438 are disposed within the ionization chamber 416 so as to be centrally aligned with the aperture 440A in the flow guide 440 in the transitional structure 420. The tip 442T of the conduit 442 is disposed in close proximity to, and in substantially planar alignment with, the interior wall 418. The body 412 of the detector 400 is preferably constructed of a two-part, generally elongate configuration, with the source chamber 414 being the first start and transitional structure 420 and the ionization chamber 416 being integrated in the second part. In the illustrated embodiment, the detector body 412 is preferably of unitary construction having the discharge and ionization chambers 414, 416 machined therein according to known construction techniques. The detector gas inlet 415, sample gas inlet 424, and vent outlet 426 may suitably be constructed to include fittings having passageways extending through the side wall of the detector body 412.

Arrows 452 are representative of the magnitude and direction of the detector gas stream; arrows 454 are similarly representative of an optional dopant or purge gas fluid stream; arrows 456 are similarly representative of the sample gas stream; arrows 458 are similarly representative of an ionized mixture of the detector gas stream, the optional dopant gas stream, and the sample gas stream. As shown in FIG. 4B, the length of an arrow is indicative of the relative linear velocity of the respective fluid stream at the location of the arrow. Accordingly, as illustrated, the linear velocity of the detector gas stream is highest in the vicinity of the aperture 440A as compared to the linear velocity of the detector gas fluid stream at points downstream in the transitional structure 420 or ionization chamber 416.

Hence, another aspect of the illustrated embodiment is that the detector gas flows rapidly through the flow guide 440 and away from the source chamber 414, due to the increase in the linear velocity of the detector gas as it proceeds through aperture 440A. The fluid flow rate of the sample gas in the vicinity of the detection zone 432 is significantly slower in comparison to the flow rate of the detector gas as it exits the aperture 440A, thus minimizing the analyte diffusion from the detection zone 432 and into the source chamber 414. Due to the expanding diameter of the flow guide 440, there is a relatively slower linear velocity of the detector gas and sample gas in the detection zone 432, compared to the linear velocity of the detector gas in the vicinity of the aperture 440A, which encourages beneficial distribution and ionization of the sample molecules in the detection zone 432.

Figure 5:
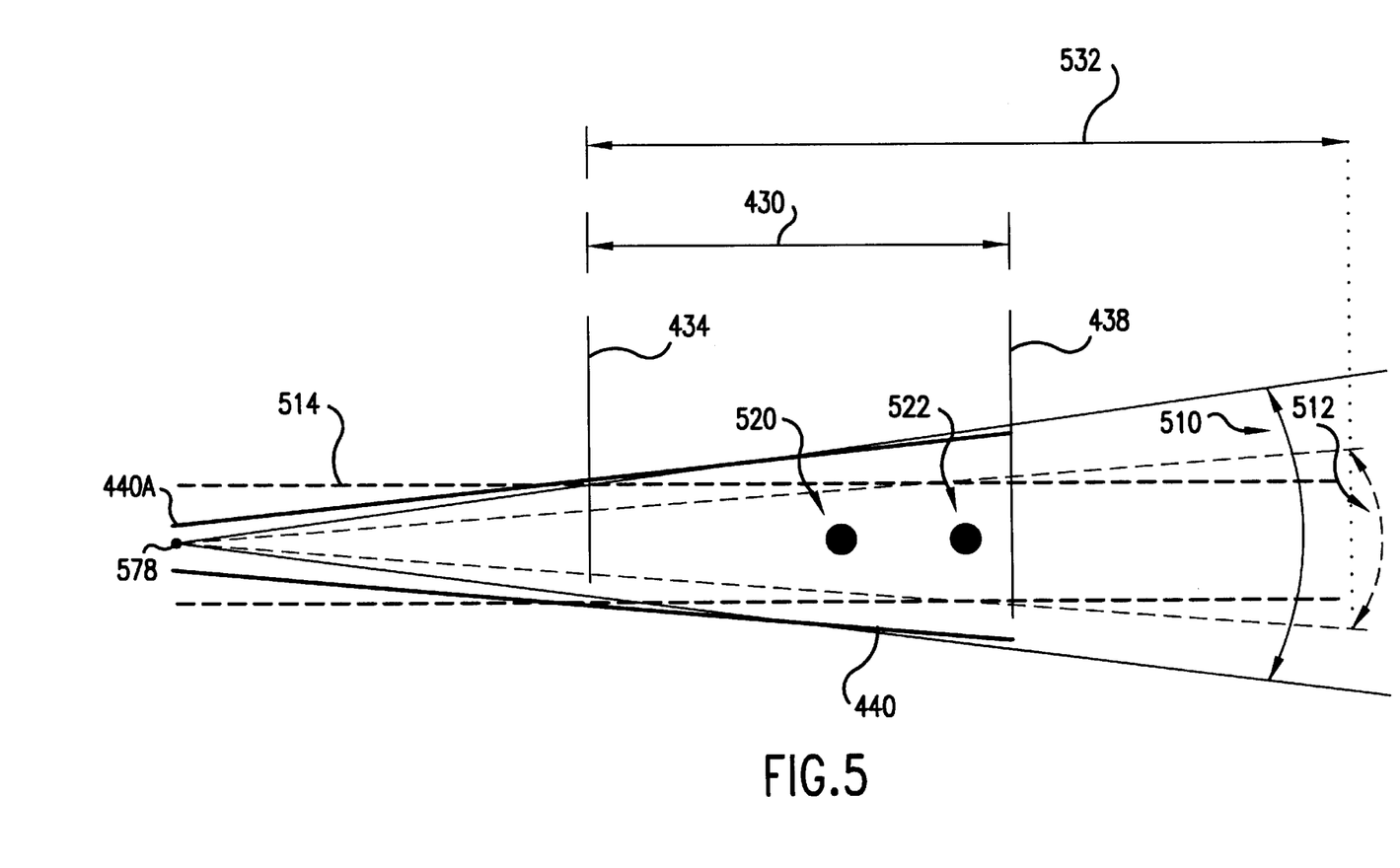
FIG. 5 is a simplified diagrammatic representation of the volumetric center and the line of sight for transition of photons in a conventional ionization detector (illustrated by dashed lines) and in an ionization detector constructed according to the present invention (illustrated by solid lines).

Referring to FIG. 5, a simplified diagrammatic view of the interior wall 418 of the flow guide 440 is illustrated. The geometry of the flow guide 440 allows an included angle of sight 510, which is preferably in the range of 10 degrees to 80 degrees and most preferably in the range of 30 degrees to 50 degrees, to be defined from a point ionization source 508 located in the plane of the aperture 440A. For comparison, there is shown an angle of sight 512 representative of a typical cylindrical ionization chamber 514 constructed according to the prior art. The geometry of the flow guide 440 thereby provides several advantages over the prior art: a) a volumetric center 520 may be located closer to the point ionization source 508 as compared to the location of a volumetric center 522 representative of the typical cylindrical ionization chamber 514; a direct line of sight traverse of photons is provided from the point ionization source 508 to the majority of the flow guide 440 and hence into the detection zone 430, the latter being much more compact than the typical detection zone 532 observed in a prior art ionization chamber; and the flow guide 440 a sufficient increase in the linear velocity of the detector gas in the aperture 440A so as to reduce or preclude analyte diffusion from the detection zone 432 toward the source chamber 414.

Figure 6:
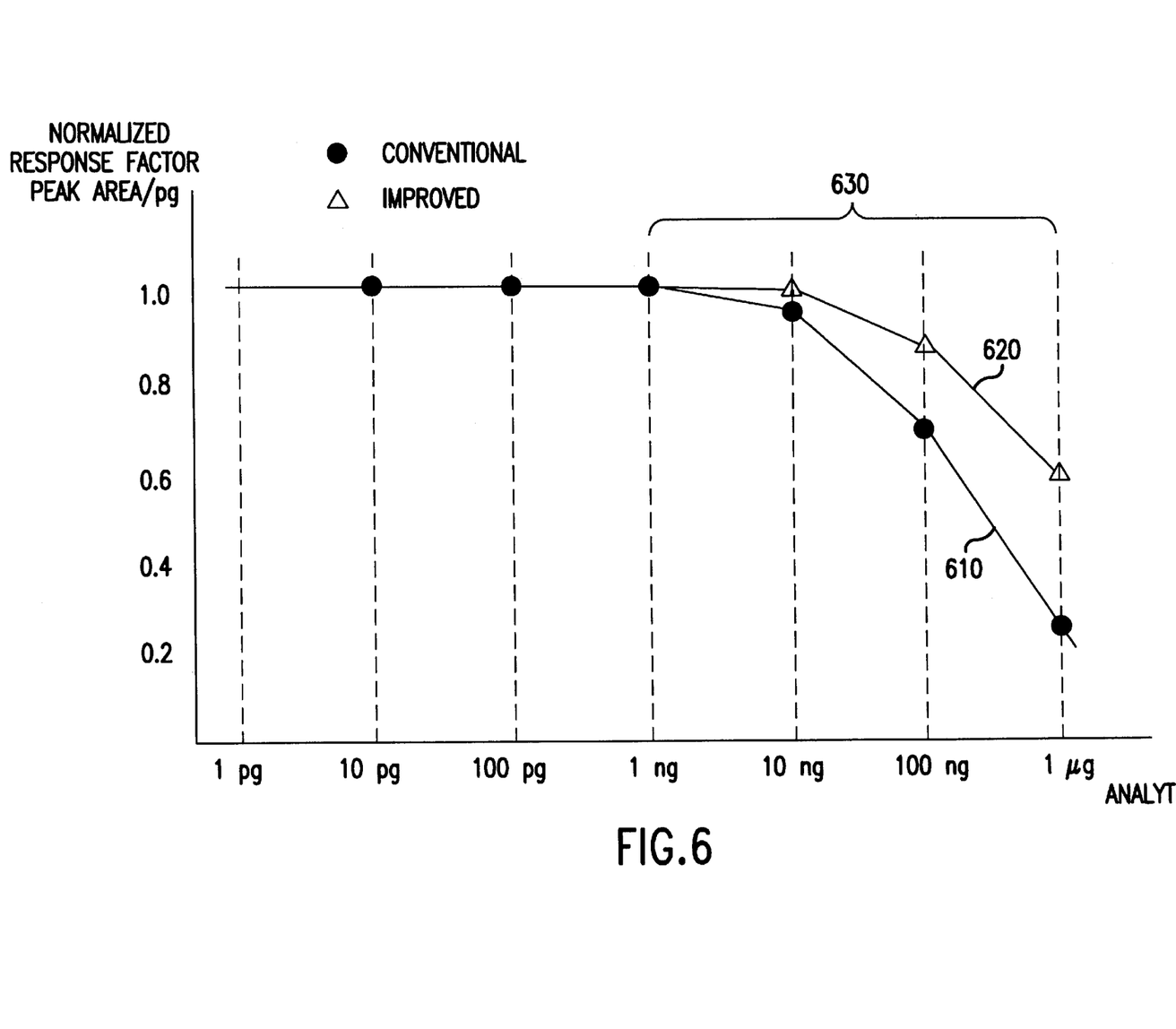
FIG. 6 is a graphical representation of an improved normalized response factor exhibited by an ionization detector constructed according to the present invention.

FIG. 6 illustrates a first plot 610 of the normalized response factor of a discharge ionization detector constructed according to the prior art, and a second plot 620 of the normalized response factor of a discharge ionization detector constructed according to the present invention. Both detectors received a sample of carbon-12. The plot 620 indicates an improved response factor that is flat in an extended response region 630 and is not subject to a significant reduction until an analyte amount greater than approximately 100 nanograms was introduced to the discharge ionization detector.

What is claimed is:

1. An ionization detector for detection of an analyte, comprising:

a source chamber having a source of ionizing particles and receiving a fluid stream of detector gas;

an ionization chamber;

an inlet connected to the ionization chamber for providing a sample gas stream containing the analyte into the ionization chamber; and a transitional structure located between the source chamber and the ionization chamber, whereby the ionization chamber is connected to the source chamber at an aperture therebetween and having a diverging bore so as to cause the detector gas to flow through the bore in the transitional structure and into the ionization chamber at a progressively decreasing linear velocity, and so as to allow the ionizing particles generated in the source chamber to be transferred to a detection zone in the ionization chamber; whereby analyte diffusion through the transitional structure is suppressed.

2. The detector of claim 1, wherein the transitional structure further comprises a flow guide provided in the form of a conical horn.

3. The detector of claim 1, wherein the transitional structure includes a predetermined aspect ratio for permitting line of sight transfer of photons from the source chamber to the detection zone prior to the onset of decay.

4. The detector of claim 1, wherein the aperture and interior surface are situated with respect to the source chamber so as to permit a line of sight for propagation of photons from a point ionization source to the detection zone in the ionization chamber, and wherein the inlet connected to the ionization chamber includes a conduit for providing the sample gas therefrom and a conduit receiving structure for locating the conduit outside of the line of sight propagation.

5. The detector of claim 1, wherein the transitional structure includes a flow guide having an aperture for causing a region of detector gas flow having a greater linear velocity than the linear velocity of the detector gas elsewherein the transitional structure, and wherein the region of detector gas flow having a greater linear velocity is located upstream of the detection zone.

6. The detector of claim 1, wherein the inlet connected to the ionization chamber includes a conduit for providing the sample gas therefrom and a conduit receiving structure for causing the direction of the effluent flow of the conduit to be transverse to the detector gas stream.

7. A discharge ionization detector for detection of an analyte, comprising:
  a source chamber;
  an ionization chamber connected to the ionization chamber;
  a discharge source in the source chamber for effecting a discharge to provide a plurality of ionizing particles;
  a first inlet for introducing detector gas flow into the source chamber;
  a second inlet for introducing a flow of sample gas containing an analyte into the ionization chamber, and a vent for venting a gas mixture from the ionization chamber;
  a signal electrode assembly located in the ionization chamber and defining a detection zone;
  a flow guide situated between the source chamber and the ionization chamber for directing detector gas flow between the source chamber and the detection zone, the flow guide being provided in the form of a conical horn so as to cause the linear velocity of the detector gas fluid stream to progressively decrease as it approaches the detection zone and to provide a line of sight transfer of photons from the discharge source to the detection zone.

8. The detector of claim 7, wherein the discharge source is provided as a point ionization source in the source chamber.

9. An ionization detector for detection of an analyte, comprising:
  a detector body defining a first chamber in the form of a source chamber and a second chamber in the form of an ionization chamber, the first and second chambers being coaxially disposed and having a common internal wall shaped as a flow guide and having a central aperture located at the transition between the first and second chambers, wherein the aperture includes input and outlet ends therein and wherein the flow guide includes a first region of high detector fluid flow rate in the vicinity of the aperture and a second region of progressively decreasing detector fluid flow in a downstream direction, the first region of high detector fluid flow rate in the vicinity of the aperture and the second region of progressively decreasing detector fluid flow in a downstream direction being situated so as to direct fluid flow in the downstream direction from the source chamber to the ionization chamber, but to suppress analyte diffusion in an opposing direction;
  an inlet in the source chamber for admitting a fluid stream of detector gas;
  an inlet in the ionization chamber for admitting a fluid stream of sample gas to be analyzed; and
  a source of ionizing particles located in the source chamber.

10. The detector of claim 9, wherein the source of ionizing particles includes an electrode assembly having at least a discharge cathode situated an insulating sleeve through the detector body so as to extend into the source chamber.

11. The detector of claim 9, wherein the source of ionizing particles includes a radioactive source material.

12. A method for detection of an analyte, comprising the steps of:
  providing a source chamber having a source of ionizing particles and receiving therein a fluid stream of detector gas;
  providing an ionization chamber;
  connecting an inlet connected to the ionization chamber for providing a sample gas stream containing the analyte into the ionization chamber; and
  locating a transitional structure between the source chamber and the ionization chamber, whereby the ionization chamber is connected to the source chamber at an aperture therebetween and includes a diverging interior surface to cause the fluid stream of detector gas to flow through the transitional structure at a progressively decreasing linear velocity and into the ionization chamber, so as to allow the ionizing particles generated in the source chamber to be transferred to the ionization chamber; whereby analyte diffusion through the transitional structure is suppressed.

* * * * *